(12) United States Patent
Troxler et al.

(10) Patent No.: US 6,567,498 B1
(45) Date of Patent: May 20, 2003

(54) LOW ACTIVITY NUCLEAR DENSITY GAUGE

(75) Inventors: Robert E. Troxler, Raleigh, NC (US); W. Linus Dep, Chapel Hill, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 10/044,202

(22) Filed: Jan. 10, 2002

(51) Int. Cl.⁷ .............................................. G01B 15/02
(52) U.S. Cl. ........................................ 378/89; 378/86
(58) Field of Search .................................. 378/86–90

(56) References Cited

U.S. PATENT DOCUMENTS

| | | |
|---|---|---|
| 2,998,527 A | 8/1961 | Shevick et al. |
| 3,544,793 A | 12/1970 | Bless et al. |
| 3,774,034 A | 11/1973 | Martin |
| 4,525,854 A | 7/1985 | Molbert et al. |
| 4,641,030 A | 2/1987 | Regimand |
| 4,701,868 A | 10/1987 | Regimand |
| 4,766,319 A | 8/1988 | Regimand |
| 5,068,883 A | * 11/1991 | DeHaan et al. ............... 378/86 |

OTHER PUBLICATIONS

Siew–Ann Tan & Tien–Fang FWA; Nondestructive Density Measurements of Cylindrical Specimens by Gamma–Ray Attenuation; Journal of Testing and Evaluation; Mar. 1991; pp. 155–160; vol. 19, No. 2.
S.V. Bodwadkar & J.C. Reis; Porosity Measurements of Core Samples using Gamma–ray Attenuation; Elsevier Science Ltd; 1994; pp. 61–78; vol. 8, No. 1; Great Britain.
C.S. Hughes; Investigation Of A Nuclear Device For Determining The Density Of Bituminous Concrete; Highway Engineer Trainee, Virginia Council of Highway Investigation and Research; pp. 401–417.
L. Dep, M. Belbot, G. Vourvopoulos, S. Sudar; Pulsed neutron–based on–line coal analysis; Journal of Radioanalytical and Nuclear Chemistry; 1998; pp. 107–112; vol. 234; Nos. 1–2; Budapest.

C.G. Clayton & C.F. Coleman; Current Developments And Applications Of Nuclear Techniques In The Coal Industry; Nuclear Geophysics Group, et al; pp. 1–4.

* cited by examiner

*Primary Examiner*—Craig E. Church
(74) *Attorney, Agent, or Firm*—Alston & Bird LLP

(57) ABSTRACT

A nuclear density gauge and test method is provided for measuring density material in a relatively thin zone beneath a surface of the material. The gauge comprises a gauge housing and a substantially planar base on said gauge housing adapted to be positioned on a surface of the material sample. A gamma radiation source having a characteristic primary energy and an activity of no more than 100 microcurie is mounted within the housing and cooperates with the base for emitting gamma radiation through the base and into an underlying material sample. An energy selective gamma radiation detector is mounted within the gauge housing and in laterally spaced apart relation from the gamma radiation source. The gamma radiation detector is operable for quantifying the energy level of the detected gamma radiation. Shielding is provided within the gauge housing between the source and the detector for preventing gamma radiation from passing directly from said source to the detector. An analyzer is connected to the detector for detecting gamma radiation counts in a predetermined energy spectrum having a lower limit of 0.1 MeV or greater and an upper limit which is less than the characteristic primary energy of said source. The density of the sample is calculated based upon the gamma radiation counts obtained by the analyzer within the predetermined energy spectrum.

47 Claims, 3 Drawing Sheets

LOW ACTIVITY NUCLEAR DENSITY GAUGE

FIELD OF THE INVENTION

This invention relates to the measurement of density, and more particularly to a test instrument and method for measuring the density of a sample using gamma radiation. The invention is especially suited for measuring the density in a relatively thin zone below the surface of a sample.

BACKGROUND OF THE INVENTION

In the asphalt pavement construction industry, portable nuclear gauges are frequently used for measuring the density of the asphalt pavement. Often, the asphalt paving material is applied in relatively thin layers, e.g. on the order of about one to two inches in thickness, over a prepared roadbed foundation or an existing paved roadway. Consequently, there is a need to measure density of the pavement sample in a relatively thin zone, e.g., one to three inches in depth, below the pavement surface. To this end, nuclear density gauges have been developed for directly measuring the density of a thin layer of paving material. For example, nuclear "thin layer" gauges of this type are described in commonly owned U.S. Pat. Nos. 4,641,030; 4,701,868 and 6,310,936. The gauges described in these patents use a Cesium-137 ($^{137}$Cs) source of gamma radiation containing approximately eight millicuries of Cesium-137. Gamma radiation that is Compton scattered from the underlying sample is detected by Geiger-Mueller tubes positioned to form two geometrically differing source-to-detector relationships, and the density of the material is calculated based upon the gamma radiation counts detected by the respective detectors.

Although the activity of the gamma radiation source in these gauges is quite small, in the millicurie range, and can be safely used by an operator with ordinary precautions and care, regulatory agencies impose restrictions on the handling, transport, storage and use of such gauges, and on persons qualified to operate such gauges. Consequently, there exists a need for a gauge which uses a radiation source of a much lower activity level which is not subject to the regulatory requirements of existing gauges.

It is therefore an object of the present invention to provide a nuclear gauge suited for measuring the density in a relatively thin zone below the surface of a sample, and which uses a low activity radiation source.

It is a more specific object of the present invention to provide a gauge which can operate using a gamma radiation source having an activity in the microcurie range, and more specifically with an activity of no more than 100 microcurie, and more desirably an activity of no more than 50 microcurie. Gauges employing these low activity nuclear sources are subject to fewer and less stringent restrictions and regulations, if any.

Prior attempts to produce nuclear gauges using low activity (microcurie) radiation sources have had limited success, primarily because of their limited levels of accuracy. By way of example, one prior nuclear gauge using a low activity nuclear source is described in commonly owned U.S. Pat. No. 4,766,319. The main difficulty in developing a gauge based on a low activity gamma radiation source is that the signal to noise ratio of the gamma radiation detection is low because of the relatively low gamma radiation flux from a low activity source. Background radiation from certain naturally occurring radioactive elements (e.g. K-40, U and Th) present in the material to be tested generate noise which cannot be ignored without sacrificing the accuracy of measurement. With conventional gauges using higher activity gamma radiation sources (e.g. a 8000 microcurie Cs-137 source), the signal to noise ratio is high and the background radiation does not contribute significant error.

SUMMARY OF THE INVENTION

The present invention provides a nuclear density gauge and method which is suited for measuring the density in a relatively thin zone beneath the surface of a sample of paving material. The gauge may be designed to measure the density in a zone up to a specific depth of, for example, up to 1 or as much as 3 inches beneath the surface of the material sample. The gauge uses one or more gamma radiation sources having a total activity of no more than 100 microcurie. The gauge includes a gauge housing having a surface adapted to be positioned on a surface of the material sample. The microcurie gamma radiation source is mounted within the housing for emitting gamma radiation through the base and into an underlying material sample. At least one energy selective gamma radiation detector is mounted within the gauge housing in spaced apart relation with respect to the gamma radiation source, with the detector being operable for producing signals representing the energy level of the detected gamma radiation. Density calculating means is connected to the detector and is operable for calculating a value for the density of the material based upon detected signals having an energy level within a predetermined portion of the energy spectrum of the gamma radiation detected by the detector. In one embodiment, the density calculating means includes an analyzer which is connected to the detector and is operable for classifying and accumulating signals from the detector into one or more channels corresponding to said predetermined portion of the energy spectrum. The analyzer may, for example, comprise a multichannel analyzer which classifies and accumulates signals in a plurality of discrete channels over the energy spectrum of the gamma radiation detected by the detector, and wherein at least one of these discrete channels defines said predetermined portion of the energy spectrum.

In one specific embodiment, the predetermined portion of the energy spectrum which is used for density calculation has a lower limit of 0.1 MeV or greater and an upper limit which is less than the characteristic primary energy of the source. The gamma radiation source may comprise at least one Cesium-137 gamma radiation source with a 0.662 MeV primary energy. Preferably, the detector is a scintillation detector, and the system may include an analyzer connected to the scintillation detector which is capable of identifying the counts which have an energy within the specified energy spectrum.

BRIEF DESCRIPTION OF THE DRAWINGS

Some of the features and advantages of the invention having been described, others will become apparent from the detailed description which follows, and from the accompanying drawings, in which.

DETAILED DESCRIPTION OF THE INVENTION

Figure 1:
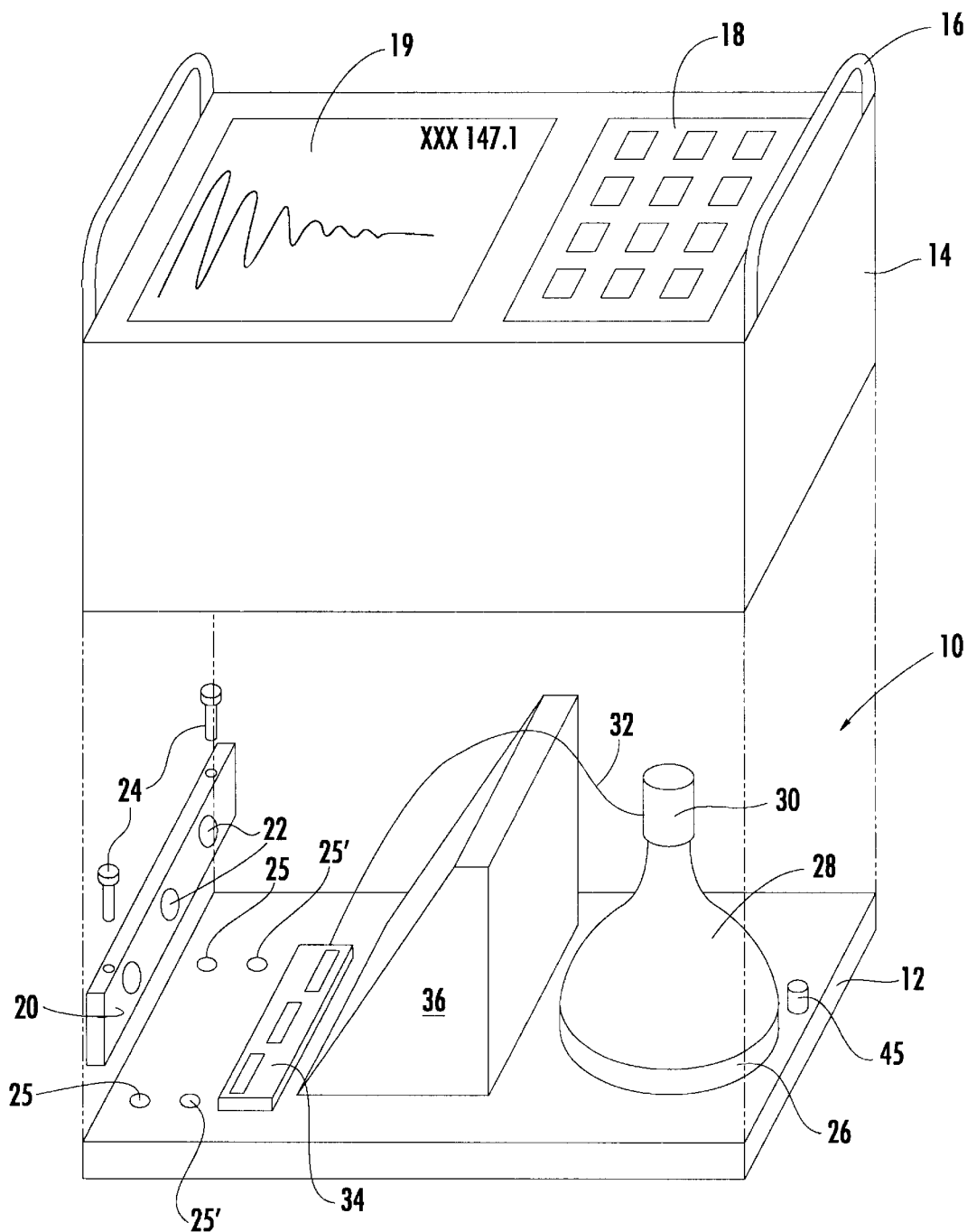
FIG. 1 is an exploded schematic view of a gauge in accordance with one embodiment of the invention.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Theory

The present invention is based on the scattering and absorption properties of gamma radiation with matter. For gamma radiation with energies less than 2 MeV, there are two dominant interacting mechanisms with matter. In the 0.1 to 2 MeV energy range, the dominant mechanism is inelastic scattering (Compton scattering). For energies less than 0.1 MeV, the dominant mechanism is photoelectric absorption. In the 0.1 to 2 MeV energy range, the amount of gamma radiation scattering (energy degradation) is a function of electron density of the material and therefore, density is a fundamental measurement property. This results in a nuclear attenuation per unit-length mass-density that is less influenced by the material composition. At energies below 0.1 MeV, the photoelectric absorption of gamma radiation is sensitive to the atomic number of the material and hence to the chemical (elemental) composition of the material. Therefore, when a gamma radiation source of sufficient energy is placed near a material, and an energy selective gamma radiation detector is used for gamma radiation detection, gamma radiation mainly undergoing Compton scattering can be counted exclusively. With proper calibration, the gamma radiation count can be converted to an absolute density.

According to one specific embodiment of the invention, a $^{137}$Cs gamma radiation source with a 0.662 MeV primary energy is used. However, other gamma radiation sources with different primary energy levels could be employed, such as $^{60}$Co for example. Gamma radiation interacting with the sample is measured with a detector, which is preferably an energy selective detector configured to detect gamma radiation in a predetermined energy spectrum. Gamma radiation detectors may be configured in various ways to be selective to a desired energy spectrum. For example, in the embodiment shown and described herein, an energy selective scintillation detector is used, specifically a sodium iodide (NaI) crystal mounted on a photomultiplier tube (PMT). When using a $^{137}$Cs source, gamma radiation interacting with the sample with energies in the predetermined range 0.1 to 0.4 MeV are counted. In a further specific embodiment, gamma radiation with energies in the predetermined range of 0.1 to 0.25 MeV are counted. The gamma radiation within this energy spectrum is that which has interacted with the underlying material and has been backscattered to the detector. Because of Compton scattering, the radiation posses a lower energy level than the 0.662 MeV primary energy of the $^{137}$Cs source. For gamma radiation sources other than $^{137}$Cs, the upper limit would be selected in a similar manner based upon the energy distribution for the particular source selected.

Apparatus

One embodiment of a gauge in accordance with the present invention is shown in FIG. 1. The gauge is indicated generally by the reference character 10. The gauge includes a base 12 having a substantially planar lower surface and a gauge housing 14 which cooperates with the base 12 to protectively enclose the various components of the gauge. A handle 16 extends upwardly from the gauge housing 14 to facilitate transporting the gauge. On the upper side of the gauge housing 14 suitable input-output devices are provided, such as the keypad 18 and display 19 shown in the drawing.

Additional components of the gauge are mounted to the upper surface of the base 12. As shown, located adjacent one longitudinal end of the base 12 is a source plate 20. Source plate 20 is in the form of an elongate bar. In the illustrated embodiment, a series of three discrete radiation point sources 22 are mounted at spaced-apart locations to one side of the source plate 20. It will be understood that more than three discrete point sources could be used. In an alternative embodiment, not illustrated, the radiation source may be continuous and distributed along the entire length of the source plate. Alternatively, the sources may be arranged in a pattern, such as a circular pattern, surrounding the detector. In any event, the total activity of the gamma radiation sources does not exceed 100 microcurie. In the particular embodiment illustrated, the gamma radiation source is Cesium-137 and each individual point source of Cesium-137 has an activity of no more than 10 microcurie.

The source plate 20 is preferably mounted so that it can be readily removed from the base plate 12. In the embodiment shown, the source plate 20 has two vertically extending holes adjacent each end which are adapted to receive threaded fasteners, such as bolts 24, and which threadably engage suitably tapped holes 25 formed in the base plate 12. This arrangement makes it possible to remove the radiation source, either for replacement or for taking background radiation counts, as explained more fully below. It also ensures that the source plate 20 is reliably and consistently located at the same position when installed on the base 12, since the distance and geometrical relationship between the source plate 20 and the radiation detector must be consistently maintained for accurate and reproducible results. For radiation safety, the source plate 20 may be tethered to the gauge to prevent loss while removed from the gauge.

An energy selective detector system is mounted to the base 12 adjacent the opposite end from the source plate 20. In the particular embodiment illustrated in FIG. 1, the energy selective gamma radiation detector system includes a sodium iodide crystal 26 and a photomultiplier tube 28 mounted to the sodium iodide crystal. When gamma radiation strikes the sodium iodide crystal, photons are released, varying in intensity corresponding to the energy level of the gamma radiation. The photomultiplier tube 28 detects the photons and converts them to electrical signals which, in turn, are amplified by an amplifier 30 mounted to the photomultiplier tube. The amplified signals are directed, via an electrical conductor 32, to a circuit board 34, where the signals are processed as described more fully below.

Radiation shielding 36 is also mounted on the base plate 12. The shielding 36 is located directly between the source plate 20 and the radiation detector assembly to inhibit gamma radiation emanating from the gamma sources 22 from passing directly from the sources to the detector. Consequently, the only gamma radiation from the sources 22 that is received by the detector is radiation which has passed through the base 12 into the underlying material sample, and which has interacted with the material sample before being scattered back upwardly through the base 12 to the sodium iodide crystal 26. Thus, the gauge operates in the "backscatter" mode. Any suitable material capable of blocking gamma radiation can be used as the shielding 36, with lead or other dense metals being typical.

Figure 2:
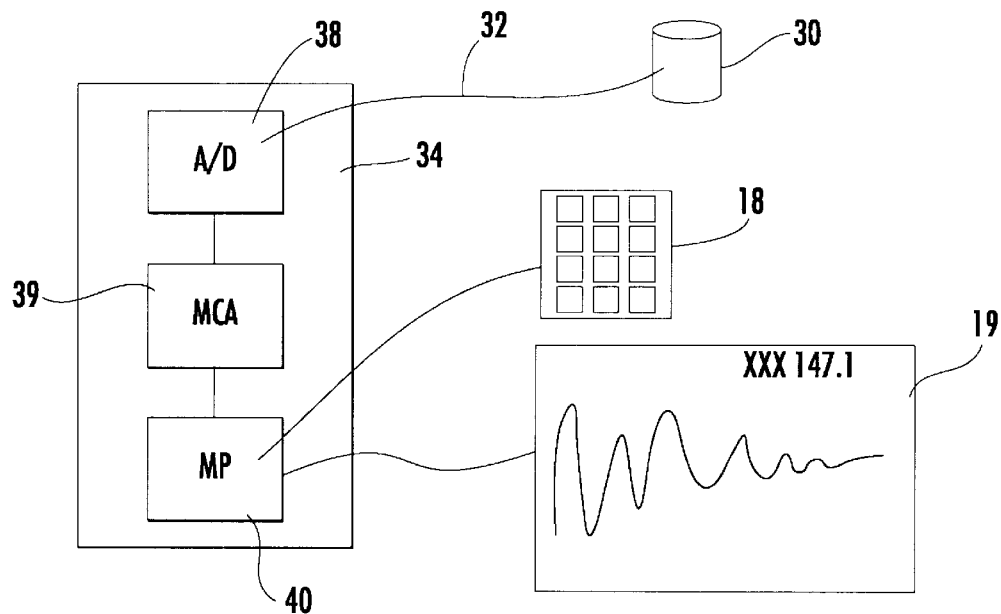
FIG. 2 is a schematic diagram showing the circuitry for processing the signals obtained by the gauge.

The functional components of the circuit board 34 are shown schematically in FIG. 2. An analog-to-digital converter 38 transforms the amplified analog signals from amplifier 30 into digital signals quantifying the energy level of the gamma radiation (photon) count. The output of the analog-to-digital converter 38 is directed to an analyzer device, which in the illustrated embodiment is a multi-channel analyzer (MCA) 39 which accumulates the number of gamma radiation (photon) counts of different energy levels into a plurality of channels, each channel corresponding to portion of the energy level spectrum. For purposes of density calculation, only a predetermined portion of the overall energy spectrum detected by the detectors is considered. Thus, only the accumulated counts from one or more of the channels corresponding to this predetermined portion are considered for the density calculation. For example, in one specific embodiment, this energy spectrum has a lower limit of 0.1 MeV and an upper limit of 0.4 MeV when a $^{137}$Cs gamma radiation source is used. In a more specific embodiment, the lower limit is 0.1 MeV and the upper limit is 0.25 MeV. Other channels of the analyzer representing other slices of the energy spectrum may be considered for taking standard counts or in compensating for background radiation. The output of the MCA 39 is directed to a processor 40 containing a set of stored instructions suitable for converting the accumulated gamma radiation (photon) counts from the MCA into a density value. The processor 40 is operatively connected to the keypad input device 18 and to the output display 19.

Preferably, the source or sources of gamma radiation are configured so that gamma radiation emanates from a laterally extending area or zone so as to provide for a number of individual of pathways along which the gamma radiation may travel downwardly into the underlying sample. The resulting backscattered radiation also travels along a number of pathways back up to the detector system. In the embodiment illustrated, there are three discrete 10 microcurie point sources of $^{137}$Cs mounted on the source plate 20, and the gamma sources are oriented along a line generally perpendicular to a line passing directly from the source plate to the detector. Since the detector is capable of receiving radiation over its entire area, there are numerous paths of travel for the gamma radiation passing downwardly into the underlying sample and being backscattered to the detector system. It will be appreciated that similar results would be achieved from a source which extends along the entire length of the source plate 20. To make more efficient use of the detector area, the detector system may include a plurality of smaller sodium iodide crystals and associated photomultiplier tubes arranged side-by-side, instead of the single crystal 26 and photomultiplier tube 28 shown in FIG. 1. By providing multiple paths of travel in this manner from the source to the detector, the gauge is able to see a larger volume of the sample and the error caused by the surface roughness of the sample is thereby reduced.

Spectrum Stabilization

Scintillation detectors are sensitive to temperature fluctuations. In the digital spectrum produced by the MCA, the energy level of the gamma radiation detected by the scintillation detector is correlated into one of many (e.g. 512) channels representing the counts corresponding to a particular gamma radiation energy level or range. This spectrum may be represented graphically as extending in the x-direction, with the total number of counts in each channel extending in the y-direction. When the temperature fluctuates, the spectrum fluctuates non linearly in the x-direction. Therefore, a peak once centered on one channel may end up centered on a different channel. If one wants to find the gamma radiation (photon) counts in channels between $C_{lower}$, representing the energy $E_{lower}$, and $C_{upper}$, representing the energy $E_{upper}$, because of these fluctuations, the counts obtained from using the "raw" spectrum will have uncertainties due to the temperature sensitivity. An analog or digital spectrum stabilizer is used to stabilize the spectral drifts resulting from temperature fluctuations in the NaI detector. For purposes of spectrum stabilization, the gauge is provided with an additional 1 microcurie $^{241}$Am gamma radiation reference source 45 mounted near the detector 26 in the embodiment shown in FIG. 1. The 0.056 MeV peak from the source 45 is used as a reference point by the MCA for stabilization of the spectrum.

During a 4 minute counting time, the MCA collects counts, which are then corrected for signal amplitude fluctuations and stored in a buffer. At the end of counting, the MCA gives the stabilized spectrum.

In an alternative approach, spectrum stabilization could be carried out without requiring an additional radiation source for reference. A tiny "leak" hole could be provided in the shielding 36 so that a small fraction of the gamma radiation can pass directly from the source 22 to the detector 26. In this instance, the 0.662 MeV peak of the gamma radiation source itself can be used as a reference point for spectrum stabilization.

Gamma Radiation Background

Figure 3:
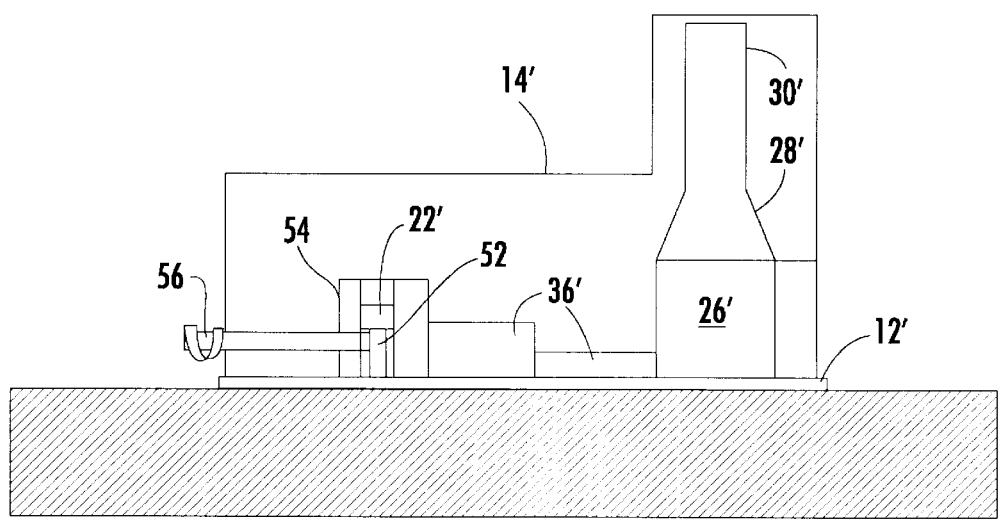
FIG. 3 is a side elevational view of a gauge in accordance with a second embodiment of the invention, shown with the source wheel in the shielded, raised position.
Figures 4, 5:
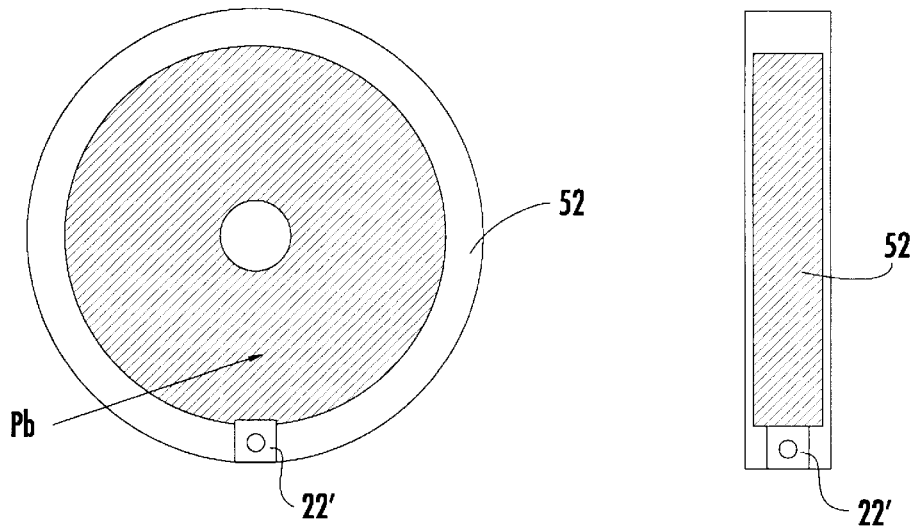
FIG. 4 is a side elevational view showing the source wheel used in the gauge of FIG. 3.
FIG. 5 is a cross-sectional view of the source wheel.
Figure 6:
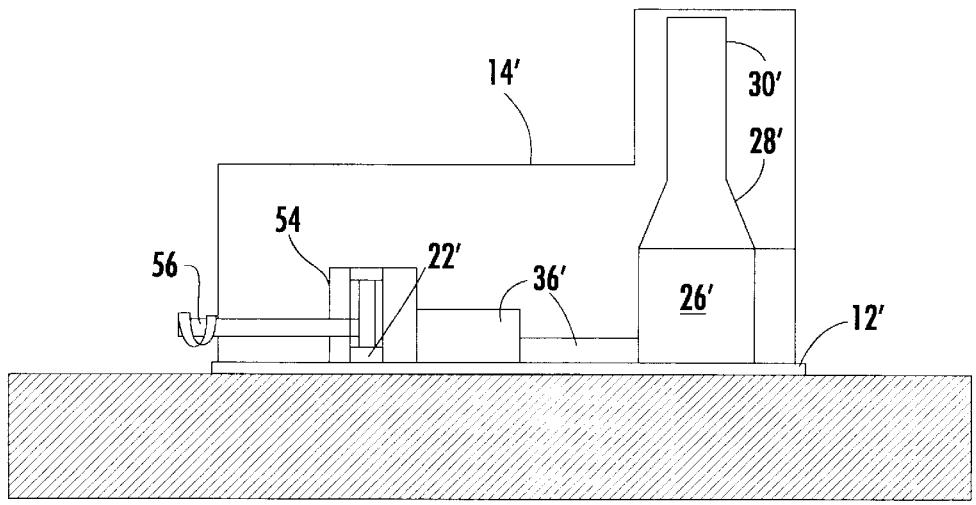
FIG. 6 is a side elevational view of the gauge of FIG. 3, shown with the source wheel in the exposed, lowered position.

In order to obtain an accurate density measurement, it is necessary to quantify the background gamma radiation from the sample and its surroundings. Conventional nuclear density gauges avoid this issue by using a stronger gamma radiation source (e.g. about 8000 micro Curie) resulting in such a large signal to noise ratio that the effect of background radiation can be ignored. With the present invention, there are several possible approaches to compensating for background gamma radiation. According to one approach, for example, the source plate 20 can be physically removed from the gauge and placed in a location shielded from the detector. Then, the sourceless gauge can be operated to obtain a gamma radiation count representing the background spectrum. According to another approach, the gauge can be constructed with a source which can be moved from an unshielded active position when operated for density measurement, to an internally shielded location within the gauge when operated for background calibration. One exemplary embodiment using this approach is illustrated in FIG. 3. To avoid repetition, like reference numbers with prime notation (') added are used to identify elements in this embodiment which correspond to elements previously described. In this embodiment, the gamma radiation source 22' is located on a disk 52 which is mounted for rotation within a shielded enclosure 54. Both the disk 52 (FIGS. 4 and 5) and the shielded enclosure 54 are made from a dense material such as lead, which is opaque to gamma radiation. A shaft 56 connected to the disk 52 extends from the gauge housing to allow for rotating the disk. When positioned in the shielded position for background counts and storage, the disk is rotated so that the source 22' is completely enclosed by the shielded enclosure, as shown in FIG. 3. When density measurements are to be taken, the shaft 56 is rotated 180° to position the source 22' in the unshielded active position shown in FIG. 6. In this position, the source 22' is located proximate to the lower surface of the base plate 12' so that gamma radiation may be directed into a material sample located beneath the base plate of the gauge.

Gamma radiation background may also be estimated "on-the-run" based upon a measurement of the gamma radiation counts having an energy level at or about 1.460 MeV. The element potassium has a long-lived radioisotope, K-40, that emits 1.460 MeV gamma radiation. Since potassium is present in the minerals typically used as the aggregate for an asphalt paving mix, Compton scattering of the 1.460 MeV gamma radiation produces background radiation in the energy spectrum which is of interest for density measurement. Another approach involves mathematical fitting of the straight-line part of the 0.662 MeV gamma radiation peak. The slope of this line can be used to estimate the background. Still another approach involves having a separate smaller detector system for background measurement. This detector may be connected to gauge electronics with a cable and placed in the side of the detector that is away from the sources, or may be placed outside the gauge enclosure.

Standard Count

Nuclear density gauges use radioactive sources having a finite half-life. The source activity decreases with time due to disintegration of nuclei. To compensate for the varying source activity, the measured gamma radiation count is normalized to the count on a standard. This count ratio is then independent of time. In conventional gauges, this standard is a polyethylene block. The present invention can employ any of several methods for acquiring a standard calibration count. For example, in one approach, the gauge can be placed on a standard plates two to three inches thick and of a surface area one or two times the footprint size of the gauge. These standard plates can be magnesium, aluminum, or a combination of magnesium and aluminum, and backscatter counts are acquired on each plate. The gamma radiation streaming from source to detector is completely stopped by the shielding, so that only a backscatter reading is acquired, and counts are taken in a particular energy window, for example 0.1–0.25 MeV (for a $^{137}$Cs source with 0.662 MeV primary energy).

In another approach, a small bore hole is formed in the shield to provide a direct path for the gamma radiation from the source to the detector so that the detector could see a direct beam of gamma radiation of 0.662 MeV energy. The net counts in the 0.662 MeV $^{137}$Cs peak can be used as the standard count, when the gauge is placed on the standard plate as well as on-the-run. Here, on-the-run means when the gauge is placed on a testing material. When the gauge is placed on the testing material, the standard count (the net counts in the 0.662 MeV primary energy) is taken simultaneously with the backscatter density count.

In still another approach, a small Geiger Muller tube is incorporated in the gauge housing near the primary source and is used to ascertain the standard count. This tube is inside the gauge and is not affected by the density of the underlying material.

Gauge Calibration Example 1

As with other nuclear gauges, the gauge has to be calibrated to convert gamma radiation counts to material bulk densities. Preliminary calibration was performed using three solid metal calibration plates: a magnesium plate with soil equivalent density of 109.8 pcf (pounds per cubic foot), a composite magnesium/aluminum plate with soil equivalent density of 133.3 pcf, and an aluminum plate with soil equivalent density of 161.2 pcf. The gauge was operated in the backscatter mode. Counts in a 0.1 to 0.25 MeV energy window were used to estimate the density. The background radiation from the sample and its surrounding was measured by obtaining counts when the $^{137}$Cs gamma radiation source was removed from the gauge. The gauge was placed on the magnesium plate and three 4-minute counts were obtained. The average of these counts was calculated as $C_{bgd1}$. The gauge was then placed on the magnesium/aluminum plate and three 4 minute counts were taken. The average count was calculated as $C_{bgd2}$. The source was reinstalled in its operative unshielded position in the gauge and the gauge was placed on the magnesium plate and three 4 minute counts were collected. The average count was calculated as $C_{Mg}$. The gauge was then placed on the composite magnesium/aluminum plate and three 4 minute counts were obtained. The average count was calculated as $C_{MgAl}$. The gauge was then placed on the aluminum plate and three 4 minute counts were collected. The average count was calculated as $C_{Al}$.

The 4 minute background count $C_{bgd}$ is given by $C_{bgd}=(C_{bgd1}+C_{bgd2})/2$. The background corrected counts on the magnesium plate was used as the standard count ($C_{std}$) where $C_{std}=C_{Mg}-C_{bgd}$.

The count ratio (CR) for each sample was then calculated using the following equation: $CR_{plate}=(C_{plate}-C_{bgd})/C_{std}$ where $C_{plate}$ is the count on a particular calibration plate. Table 1 shows the data.

TABLE 1

| Plate | Density | 4-min count | 4-min background | Count Ratio |
|---|---|---|---|---|
| Mg | 109.8 | 574525 | 40458 | 1.000 |
| Mg/Al | 133.3 | 562293 | 41798 | 0.9771 |
| Al | 161.2 | 548285 | — | 0.0508 |

The calibration counts are used to determine the calibration constants by fitting to a standard equation of the form $$CR=Ae^{-BD}-C$$

Where A, B, and C are the fitting coefficients or calibration constants and D is density.

The best fit gave the following values for the three calibration constants.

A=0.8245

B=1.4036e-3 and

C=−0.2932

Gauge Calibration Example 2

A portable calibration unit can be produced with sandwiched 1-inch thick Mg and 1-inch thick Aluminum plates. The 1-inch plate of Mg itself is formed by two 0.5-inch plates. The plates preferably have a surface area about one to two times the footprint of the gauge.

Background Count: Place the plates flat on the ground with the 1-inch Mg plate facing up. Place the gauge, with the source removed or in the shielded position, on the plate. Acquire counts for 4 minutes ($C_{bgd}$).

Standard Count: Place the plates flat on the ground with the 1-inch Mg plate facing up. Place the gauge, with the source install or in the unshielded operative position, on the plate. Acquire counts for 4 minutes ($C_{std,raw}$). The standard count $C_{std}=C_{std,raw}-C_{bgd}$.

Mg Count for Calibration: $C_{Mg}=C_{std}$.

MgAl Count for Calibration: Now remove the top 0.5-inch Mg plate. Place the gauge, with source installed and active, on the plate and acquire counts for 4 minutes ($C_{MgAl,raw}$). MgAl Count $C_{MgAl}=C_{MgAl,raw}-C_{bgd}$.

Al Count for Calibration: Now turn the plates so that the 1-inch Al plate is facing up. Place the gauge, with source installed and active, on the plate and acquire counts for 4 minutes ($C_{Al,raw}$). Al Count $C_{Al}=C_{Al,raw}-C_{bgd}$.

The counts as acquired above may now be used as described in Calibration Example 1 to obtain calibration constants.

Density Calculation

The calculation of the density of a material sample is preferably carried out by a suitably programmed microprocessor or by any other functionally equivalent device, such as an application specific integrated circuit or a general purpose computer. The gauge is placed on the sample to be measured and a count is obtained for a suitable period of time, such as 2 to 4 minutes. From the MCA, stabilized counts for the particular portion of the energy spectrum of interest are obtained. Then using the density equation and calibration constants obtained as described in the Calibration Examples above, a value for the density of the sample may be obtained. This value is displayed to the user on the display 19 of the gauge.

In a preferred implementation of this method, the calculations are carried out on the accumulated gamma radiation (photon) counts repeatedly at a frequent intervals as the counting proceeds, such as every one to two seconds, treating each as a frequency packet, and a digital filtering algorithm is utilized to decrease the statistical variation of the packet. Instead of waiting until the end of a 2 to 4 minute count to display the density value, this approach makes it possible to provide to the user an almost real-time display of the calculated density value while the count is still proceeding. The density values may be displayed to the user graphically as a function of time, as shown in FIG. 1. As the digitally filtered density value settles down to a steady state, the user may decide to accept the calculated density value as being sufficiently accurate, and to discontinue the measurement procedure without waiting until the end of the full two or four minute count. Thus, this calculation method can reduce the time required for taking density measurements and can thereby increase efficiency and productivity.

According to a further modified embodiment of the invention, it is possible for the user to adjust or to set the depth of field of the gauge so that density measurements can be obtained from a specific depth into the underlying material, such as a depth of up to one inch or up to three inches. This is achieved by adjusting the source to detector geometry. In particular, in this modified embodiment, the source can be adjustably positioned at one of several different distances from the gauge. In the embodiment shown in FIG. 1, this can be achieved by fastening the source plate 20 to the base 12 at one of several different preselected locations, provided by alternative sets of tapped holes 25' in the base for receiving the bolts 24 used to fasten the source plate. Alternatively, the location of the detector could be adjusted in relation to a fixed source location.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A nuclear gauge for measuring the density of a material, said gauge comprising:
   a gauge housing having a surface adapted to be positioned on a surface of the material sample;
   at least one gamma radiation source within said gauge housing having a characteristic primary energy and having a total activity of no more than 100 microcuries, said at least one source being positioned for emitting gamma radiation through said housing surface and into an underlying material sample;
   at least one energy selective gamma radiation detector mounted within the gauge housing in spaced apart relation with respect to said at least one gamma radiation source, said gamma radiation detector being operable for producing signals representing the energy level of detected gamma radiation; and
   density calculating means connected to said detector and operable for calculating a value for the density of the material sample based upon detected signals having an energy level within a predetermined portion of the energy spectrum of the gamma radiation detected by said at least one detector.

2. A gauge according to claim 1, wherein said density calculating means includes an analyzer connected to said at least one detector and operable for receiving said signals therefrom, said analyzer including means for classifying and accumulating signals in one or more channels corresponding to said predetermined portion of the energy spectrum.

3. A gauge according to claim 2, wherein said analyzer is a multichannel analyzer for classifying and accumulating signals in a plurality of discrete channels over the energy spectrum of the gamma radiation detected by said at least one detector, and wherein at least one of said discrete channels defines said predetermined portion of the energy spectrum.

4. A gauge according to claim 1, wherein said predetermined portion of the energy spectrum of the gamma radiation has a lower limit of 0.1 MeV and an upper limit which is less than the characteristic primary energy of said source.

5. A gauge according to claim 4, wherein said at least one source comprises at least one Cesium-137 gamma radiation source with a 0.662 MeV primary energy.

6. A gauge according to claim 5, wherein said predetermined energy spectrum falls within the range of from 0.1 MeV to 0.4 MeV.

7. A gauge according to claim 5, wherein said predetermined energy spectrum falls within the range of from 0.1 MeV to 0.25 MeV.

8. A gauge according to claim 1, wherein said at least one gamma radiation source comprises a plurality of point sources, each in spaced apart relation from one another and from said detector.

9. A gauge according to claim 8, wherein said point sources are arranged in a common plane substantially parallel to said base.

10. A gauge according to claim 1 wherein said at least one energy selective gamma radiation detector comprises a sodium iodide crystal and a photomultiplier tube operatively associated with said crystal.

11. A gauge according to claim 1 including an additional gamma radiation source having a characteristic primary energy and an activity of no more than 50 microcurie, said additional source being mounted within said gauge housing and positioned so that gamma radiation can pass directly from said additional source to said detector.

12. A gauge according to claim 1, additionally including background radiation detection means operable for calculating a value representing the ambient background gamma radiation, and wherein said density calculating means cooperates with the background radiation detection means for calculating a value for the density of the material sample which is corrected for ambient background radiation.

13. A gauge according to claim 12, wherein said background radiation detection means includes means to permit placement of said at least one source in a location shielded from said detector so that the detector can detect gamma radiation originating other than from said source.

14. A gauge according to claim 2, additionally including stabilization means associated with said analyzer for correcting for temperature sensitivity of said detector.

15. A gauge according to claim 14, wherein said stabilization means includes means responsive to reference signals in at least one other selected channel of said analyzer, said at least one other selected channel representing an energy level outside of said predetermined portion of the energy spectrum.

16. A gauge according to claim 15, wherein said stabilization means includes an additional gamma radiation source having a characteristic primary energy different from that of said at least one source, and wherein said at least one other selected channel corresponds to the characteristic primary energy of said additional source.

17. A gauge according to claim 1, including a shielded enclosure located within said housing and a disk rotatably mounted within the shielded enclosure, and wherein said gamma radiation source is mounted to said disk, the disk being rotatable to move the source from a retracted shielded position within the shielded enclosure to an exposed position for measurement.

18. A gauge according to claim 1, wherein said density calculating means includes means operable for calculating density values repeatedly during a predetermined counting time, and including a display device cooperating with said density calculating means and operable for displaying the calculated density values as a function of time during said predetermined counting time.

19. A nuclear gauge for measuring the density of a material, said gauge comprising:

a gauge housing;

a base on said gauge housing adapted to be positioned on a surface of the material sample;

at least one gamma radiation source within said gauge housing having a characteristic primary energy and having a total activity of no more than 100 microcuries, said at least one source being positioned for emitting gamma radiation through said base and into an underlying material sample;

at least one energy selective gamma radiation detector mounted within the gauge housing in spaced apart relation with respect to said at least one gamma radiation source, said gamma radiation detector being operable for producing signals representing the energy level of detected gamma radiation;

shielding within said gauge housing and located between said at least one source and said at least one detector for blocking gamma radiation from passing directly from said source to said detector;

an analyzer operatively connected to said detector for receiving said signals therefrom, said analyzer including means for classifying and accumulating signals in one or more channels over the energy spectrum of the detected gamma radiation; and density calculating means connected to said analyzer and operable for calculating a value for the density of the material sample based upon the accumulated signals in one or more of said channels selected to represent a predetermined portion of the energy spectrum of the gamma radiation detected by said at least one detector.

20. A gauge according to claim 19, wherein both said source and said detector are mounted to said base.

21. A gauge according to claim 20, including a mounting plate upon which said at least one source is located, the mounting plate being detachably connected to a predetermined location on said base to permit removing the source from the gauge housing.

22. A gauge according to claim 21, including a tether connecting the source plate to said base so that it cannot become lost or separated when removed from said base.

23. A gauge according to claim 19, including a shielded enclosure located within said housing and a movable source mount within the shielded enclosure, the source mount allowing movement of the source from a retracted shielded position within the shielded enclosure to an exposed unshielded position for taking measurements.

24. A gauge according to claim 19, wherein said at least one detector comprises a scintillation detector.

25. A gauge according to claim 24, wherein said scintillation detector comprises a sodium iodide crystal and a photomultiplier tube operatively associated with said crystal.

26. A gauge according to claim 19, wherein said detector comprises first and second scintillation detectors positioned within said housing at two geometrically differing source-to-detector relationships.

27. A gauge according to claim 26, including means for adjusting the source-to-detector spacing of at least one of said first and second scintillation detectors.

28. A gauge according to claim 19, including an additional gamma radiation source having a characteristic energy and an activity of no more than 50 microcurie, said additional source being mounted within said gauge housing and positioned so that gamma radiation can pass directly from said additional source to said detector.

29. A gauge according to claim 19, including a channel formed in said shielding for providing a path for gamma radiation to pass directly from said at least one gamma radiation source to said detector.

30. A nuclear gauge for measuring the density of a material, said gauge comprising:

a gauge housing;

a base on said gauge housing adapted to be positioned on a surface of the material sample;

at least one gamma radiation source within said gauge housing having a characteristic primary energy and having a total activity of no more than 100 microcuries, said at least one source being positioned for emitting gamma radiation through said base and into an underlying material sample;

at least one energy selective gamma radiation detector mounted within the gauge housing in spaced apart relation with respect to said at least one gamma radiation source, said gamma radiation detector being operable for producing signals representing the energy level of detected gamma radiation;

shielding within said gauge housing and located between said at least one source and said detector for blocking gamma radiation from passing directly from said source to said detector;

an analyzer operatively connected to said detector for receiving said signals therefrom, said analyzer including means for classifying and accumulating signals in one or more channels over the energy spectrum of the detected gamma radiation;

background radiation detection means connected to said analyzer and operable for calculating a value representing the ambient background gamma radiation, density calculating means connected to said analyzer and operable for calculating a value for the density of the material sample based upon the accumulated signals in one or more of said channels selected to represent a predetermined portion of the energy spectrum of the gamma radiation detected by said at least one detector, and wherein said density calculating means also cooperates with said background radiation detection means for calculating a value for the density of the material sample which is corrected for ambient background radiation; and stabilization means associated with said analyzer for correcting for temperature sensitivity of said detector, said stabilization means including means responsive to reference signals in at least one other selected channel of said analyzer, said at least one other selected channel representing an energy level outside of said predetermined portion of the energy spectrum.

31. A gauge according to claim 30, wherein said stabilization means includes an additional gamma radiation source having a characteristic energy different from that of said at least one source and having an activity of no more than 50 microcurie, said additional source being mounted within said gauge housing and positioned so that gamma radiation can pass directly from said additional source to said detector to thereby produce said reference signals, and wherein said means responsive to reference signals is responsive to the characteristic energy level of said additional gamma radiation source.

32. A gauge according to claim 30, wherein said stabilization means includes a channel formed in said shielding for providing a path for gamma radiation to pass directly from said at least one gamma radiation source to said detector to thereby produce said reference signals, and wherein said means responsive to reference signals is responsive to the characteristic energy level of said at least one gamma radiation source.

33. A gauge according to claim 30, including a shielded enclosure located within said housing and a movable source mount within the shielded enclosure, the source mount allowing movement of the source from a retracted shielded position within the shielded enclosure for taking background radiation measurements to an exposed unshielded position for taking density measurements of the material.

34. A nuclear gauge for measuring the density of a material, said gauge comprising:

a gauge housing;

a base on said gauge housing having a lower surface adapted to be positioned on an exposed upper surface of the material sample;

at least one gamma radiation source having a characteristic primary energy and a total activity of no more than 100 microcurie, said at least one source being mounted within said housing and cooperating with said base for emitting gamma radiation through the base and into an underlying material sample;

a sodium iodide crystal gamma radiation detector mounted within the gauge housing and in spaced apart relation from said gamma radiation source, a photomultiplier tube operably connected to said sodium iodide crystal detector and being operable for generating an electrical signal proportional to the energy of the gamma radiation detected by said sodium iodide detector;

shielding within said gauge housing and located between said source and said detector for shielding gamma radiation from passing directly from said source to said detector;

an analyzer connected to said photomultiplier tube and operable for detecting gamma radiation counts in one or more channels over the energy spectrum of the detected gamma radiation; and density calculating means connected to said analyzer and operable for calculating a value for the density of the material sample based upon the accumulated signals in one or more of said channels selected to represent a predetermined energy spectrum having a lower limit of 0.1 MeV or greater and an upper limit which is less than the characteristic primary energy of said source.

35. A gauge according to claim 34, wherein said source comprises a $^{137}$Cs gamma radiation source with a 0.662 MeV primary energy and an activity of no more than 50 microcurie.

36. A gauge according to claim 34, including an additional gamma radiation source having a characteristic primary energy and an activity of no more than 10 microcurie, said additional source being mounted within said gauge housing and positioned so that gamma radiation can pass directly from said additional source to said detector, and wherein said analyzer comprises a digital multichannel analyzer having a spectrum stabilizer utilizing the primary energy peak of said additional source.

37. A gauge according to claim 34 including a bore hole formed in said shielding for providing a path for gamma radiation to pass directly from said source to said detector.

38. A gauge according to claim 34 including a source plate removably mounted to said base, and wherein said gamma radiation source comprises a plurality of discrete sources, each having an activity of no more than 10 microcurie and being mounted to said source plate spaced apart from one another.

39. A gauge according to claim 34 including a shielded enclosure mounted within said housing, and source holder associated with the shielded enclosure and upon which said source is mounted, said source holder being mounted for moving the source between a retracted shielded position located within the shielded enclosure and an exposed operative position where gamma radiation may pass through said base.

40. A method for measuring the density of a material, comprising:

directing gamma radiation into the material from at least one source having a characteristic primary energy and a total activity of no more than 100 microcuries;

detecting gamma radiation which has interacted with and been backscattered by the material and quantifying the energy levels of the detected gamma radiation;

selecting gamma radiation counts having an energy level within a predetermined portion of the energy spectrum of the detected gamma radiation; and calculating a value for the density of the sample based upon the selected gamma radiation counts within said predetermined portion of the energy spectrum.

41. A method according to claim 40, wherein said step of detecting gamma radiation comprises generating signals representing the energy levels of detected gamma radiation; and wherein said step of selecting gamma radiation counts comprises classifying and accumulating the signals in one or more channels of an analyzer over the energy spectrum of the detected gamma radiation; and selecting one or more of the channels representing only a predetermined portion of the energy spectrum of the gamma radiation.

42. A method according to claim 41, wherein said step of selecting one or more channels comprises selecting channels representing gamma radiation with an energy having a lower limit of 0.1 MeV and an upper limit which is less than the characteristic primary energy of said source.

43. A method according to claim 42, wherein the source is Cesium-137 with a 0.662 MeV primary energy, and said step of selecting comprises selecting channels representing gamma radiation with an energy of from 0.1 MeV to 0.4 MeV.

44. A method according to claim 42, additionally including detecting background radiation and correcting the value for the density of the material sample to account for ambient background radiation.

45. A method for measuring the density of a material, comprising:

directing gamma radiation into the material from at least one source having a characteristic primary energy and a total activity of no more than 100 microcurie;

detecting gamma radiation which has interacted with and been backscattered by the material and generating signals representing the energy level of the detected gamma radiation;

classifying the signals according to their energy level and accumulating signal counts in respective channels of an analyzer;

selecting accumulated signals in one or more selected channels of the analyzer representing a predetermined portion of the energy spectrum of the detected gamma radiation; and calculating a value for the density of the sample based upon the selected accumulated signals; and, displaying a calculated density value for the material.

46. A method according to claim 45, wherein said step of classifying and accumulating signals is carried out over a predetermined period of time, and wherein said calculating step and said displaying step are carried out repeatedly during said predetermined period of time.

47. A method according to claim 45, wherein said calculating step includes the step of digitally filtering the signals to decrease the statistical variation in the calculated density values.

* * * * *